(12) United States Patent
Nix et al.

(10) Patent No.: US 6,176,822 B1
(45) Date of Patent: *Jan. 23, 2001

(54) INTRACARDIAC BLOOD PUMP

(75) Inventors: Christoph Nix, Aachen; Thorsten Siess, Wuerselen, both of (DE)

(73) Assignee: Impella Cardiotechnik GmbH, Aachen (DE)

(*) Notice: Under 35 U.S.C. 154(b), the term of this patent shall be extended for 0 days.

This patent is subject to a terminal disclaimer.

(21) Appl. No.: 09/194,521

(22) PCT Filed: Mar. 31, 1998

(86) PCT No.: PCT/EP98/01866

§ 371 Date: Nov. 24, 1998

§ 102(e) Date: Nov. 24, 1998

(87) PCT Pub. No.: WO98/43688

PCT Pub. Date: Oct. 8, 1998

(51) Int. Cl.⁷ ........................................ A61M 1/12
(52) U.S. Cl. .................. 600/17; 623/3; 415/900; 604/65
(58) Field of Search ............... 417/44.2, 423.14, 417/423.1, 423.3; 415/900; 600/16–18; 623/3; 604/65

(56) References Cited

U.S. PATENT DOCUMENTS

| | | |
|---|---|---|
| 3,568,659 | 3/1971 | Karnegis . |
| 3,995,617 | 12/1976 | Watkins et al. . |
| 4,382,199 | 5/1983 | Isaacson . |
| 4,512,726 * | 4/1985 | Strimling ........................ 417/412 |
| 4,688,998 | 8/1987 | Olsen et al. . |
| 4,704,121 | 11/1987 | Moise . |
| 4,779,614 | 10/1988 | Moise . |
| 4,817,586 | 4/1989 | Wampler . |
| 4,846,152 | 7/1989 | Wampler et al. . |
| 4,895,557 | 1/1990 | Moise et al. . |

(List continued on next page.)

FOREIGN PATENT DOCUMENTS 91103427   6/1991   (EP) .

OTHER PUBLICATIONS

Article: Control of Rotary Pulsatile Cardiac Assist Pump Driven by an Electric Motor; Publication date Oct. 29, 1992.
Article: Development of a Miniature Intraventricular Axial Flow Blood Pump, Publication date Jul./Sep. 1993 issue of ASAIO Journal.

* cited by examiner

Primary Examiner—Wynn Wood Coggins
Assistant Examiner—Deborah Blyveis
(74) Attorney, Agent, or Firm—Fulwider Patton Lee & Utecht, LLP

(57) ABSTRACT

A blood pump comprises a drive portion (11) and a pump portion (12) prolongated by a flexible hose (13). Pressure sensors (60, 61) determine the differential pressure between the inlet side and the outlet side of the pump. The volume flow can be determined from the differential pressure in conjunction with the rotational speed. Further, the differential pressure may be used to find the correct position of the pump in the heart. As an alternative to measuring the differential pressure, the motor current consumed by the motor (21) is measured and the volume flow of the pump is calculated therefrom under consideration of the known rotational speed. The signal from the pressure measuring device or the motor current may be used to establish the correct position of the pump in the heart.

13 Claims, 5 Drawing Sheets

U.S. PATENT DOCUMENTS

Figure 1:
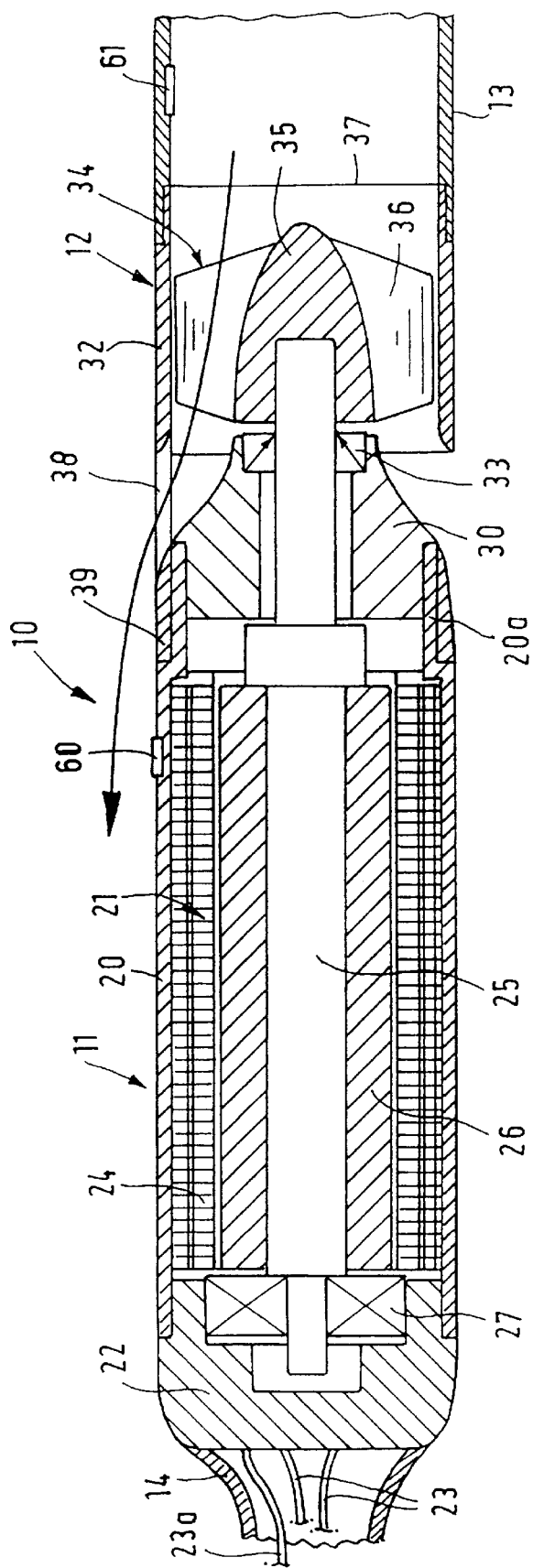

| | | |
|---|---|---|
| 4,906,229 | 3/1990 | Wampler . |
| 4,908,012 | 3/1990 | Moise et al. . |
| 4,919,647 | 4/1990 | Nash . |
| 4,944,722 | 7/1990 | Carriker et al. . |
| 5,061,256 | 10/1991 | Wampler . |
| 5,092,879 | 3/1992 | Jarvik . |
| 5,112,292 | 5/1992 | Hwang et al. . |
| 5,376,114 | 12/1994 | Jarvik . |
| 5,385,454 | 1/1995 | Kopbayashi et al. . |
| 5,385,581 | 1/1995 | Bramm et al. . |
| 5,393,207 | 2/1995 | Maher et al. . |
| 5,507,629 | 4/1996 | Jarvik . |
| 5,527,159 | 6/1996 | Bozeman, Jr. et al. . |
| 5,695,471 | 12/1997 | Wampler . |
| 5,911,685 | 6/1999 | Siess et al. . |
| 5,921,913 | 7/1999 | Siess . |
| 5,964,694 | 10/1999 | Siess et al. . |

INTRACARDIAC BLOOD PUMP

The invention relates to an intracardiac blood pump, and in particular to a blood pump that may be inserted entirely into the heart to assist the natural cardiac pump function or to replace the same by a continuous pumping operation.

A pump device for supporting the heart is described in WO94/09835 (Jarvik). This pump device comprises two independent pumps each having a pump portion and a drive portion rigidly connected therewith. The pump portion of the one pump is introduced into the left ventricle through an operation opening at the apex of the heart such that it delivers blood from the left ventricle into the aorta. The other pump portion is introduced through another operation opening into the right ventricle such that it delivers blood from the right ventricle into the pulmonary artery. The system further comprises a control and display module that is small enough to be sterilized and used in the sterile environment of the operation. It may include a microprocessor with control and monitoring algorithms for regulating the volume flow and the pressure, or to supply the volume flow and the pressure to a data base, the values thereof having been measured by sensors or having been calculated by comparing the measurements of velocity and energy consumption. These pumps, referred to as cannula pumps, may be equipped with built-in pressure sensors or volume flow measuring devices to take local measurements of these parameters in the context of patient management.

It is an object of the present invention to provide an intracardiac blood pump, the operational behavior of which can be determined with simple measuring means that require little additional space.

According to the invention, the object is solved with the features of claim 1.

In the blood pump of the present invention, the rotational speed of the motor is controlled in dependance on the pressure prevailing at the outlet side of the pump. The pressure at the delivery side of the pump is an important parameter for the output and the operating point of the pump; it may further be used to measure the volume flow, that is the yield per unit of time. The motor may be controlled such that its rotational speed is varied as a function of the measurement result of the pressure measuring means.

In the context of the present invention, the term "intracardiac" is meant to refer to the ventricles, the vestibules and the adjacent vascular stumps.

The pressure measuring means may further be used to determine the position of the pump in the heart.

Suitably, the pressure measuring means comprises two pressure sensors, one of which measures the pressure at the delivery side of the pump, while the other measures the pressure at the inlet side of the pump, the control unit controlling the rotational speed of the motor as a function of the signals from both pressure sensors. Using the pressure sensors, the differential pressure between the intake side and the delivery side of the pump is determined. From the differential pressure of the pump and the rotational speed of the motor, the volume flow may be calculated with the use of a hydraulic characteristic pumping diagram of the pump. Thus, the volume flow delivered by the pump is obtained from a very simple measurement, with the sensors requiring very little space.

Instead of two pressure sensors, a single differential pressure sensor may be provided that measures the differential pressure between the delivery side and the intake side of the pump. Such a differential pressure sensor does not provide an absolute pressure value, but rather yields a value of the differential pressure which is the essential value for determining the volume flow. On the other hand, such a differential pressure sensor may at the same time be used for locating the pump within the heart.

The pressure measuring means need not have one or more pressure sensors. Rather, the pressure may also be determined indirectly via a current measuring means that measures the motor current and calculates the differential pressure between the delivery side and the intake side of the pump from the motor current and the rotational speed.

The present invention further relates to an intracardiac blood pump offering the possibility to monitor the positioning of the pump in the heart without requiring any x-ray control for that purpose. A blood pump of this type is defined in claim 6. A measuring means provides an information signal corresponding to the differential pressure between the delivery side and the intake side of the pump. On a display device, either the information signal or a signal derived therefrom or information on the correct positioning of the pump in the heart are displayed. Here, use is made of the fact that a differential pressure between two different locations of the pump can occur only, if between these two locations, there is an element enclosing the pump, e.g. a cardiac valve. As long as there is no differential pressure between these two locations, the pump as a whole is in the same space. A differential pressure will appear only when a part of the pump is in another space. Due to this fact, the position of he pump may be determined by simple means.

Preferably, the pump is designed as an intravascular pump as described in WO97/37696 (published posteriorly). Such an intravascular blood pump is connected to a catheter. It is small enough to be pushed through a blood vessel to the place where it is intended to work, or it may also be operated in the blood vessel. In an intravascular blood pump of this type, the pump portion and the drive portion have substantially the same diameter of no more than about 5–7 mm, since the vessel width in peripheral regions of the body is slightly larger than 7 mm at most. The rigid length of such a pump must not be greater than about 35 mm so that the pump can manage to pass through bends of blood vessels. However, the pump may further be prolonged by means of a flexible hose that increases the effective length of the pump.

On the other hand, it is possible to surgically introduce the pump into the heart via the vessel system near the heart. In any case, the pump is small enough to fit into the heart, including the vestibules and the adjacent vascular stumps, and to be operated in the heart without parts of the pump extending from the heart. If any, the catheter connected to the pump is lead out from the heart. This catheter not only includes the lines for supplying electric energy to the pump, but also the signal lines leading from the sensors of the pump to the extracorporeal control unit.

The following is a detailed description of embodiments of the present invention taken in conjunction with the accompanying drawings.

Figure 2:
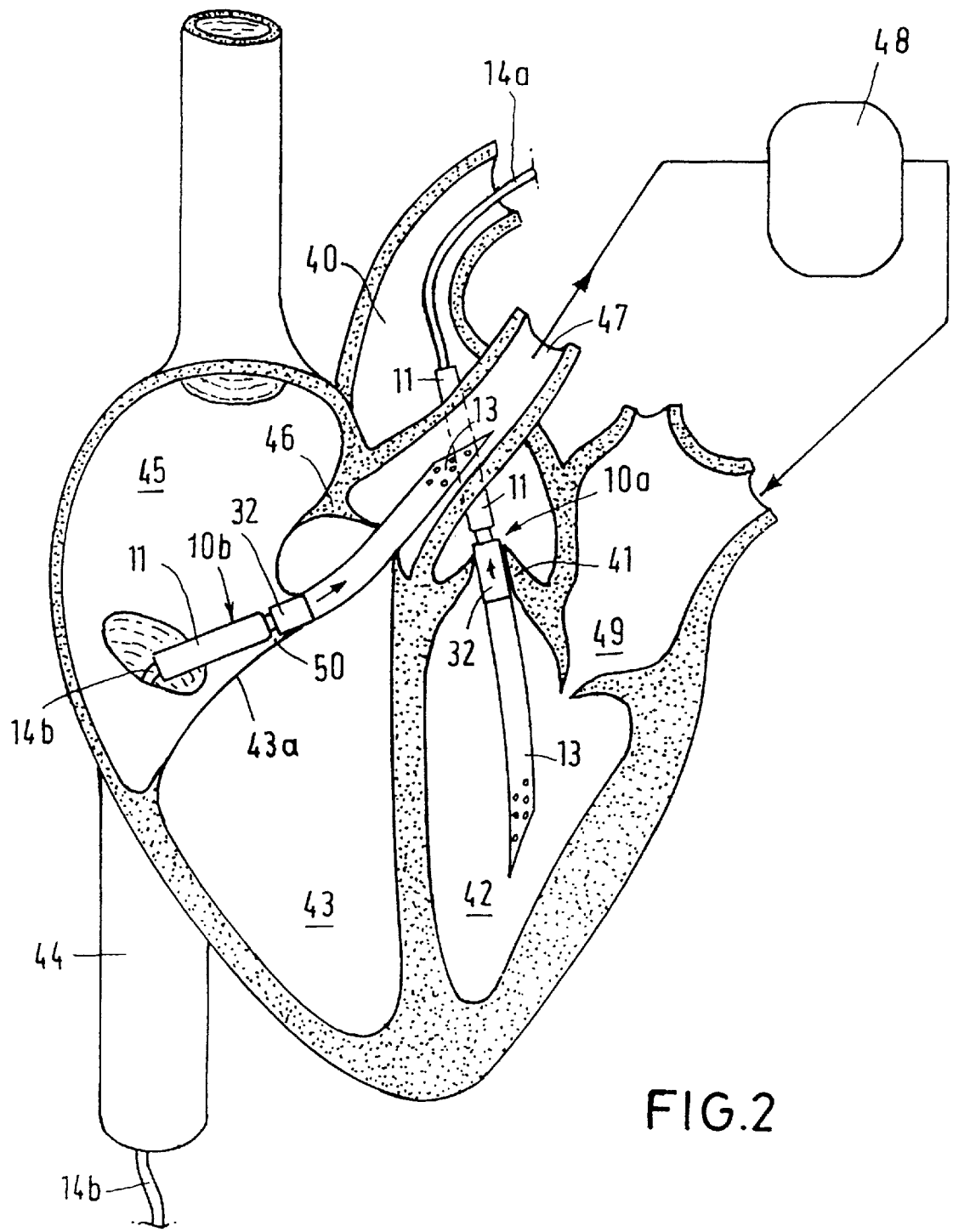
Figure 3:
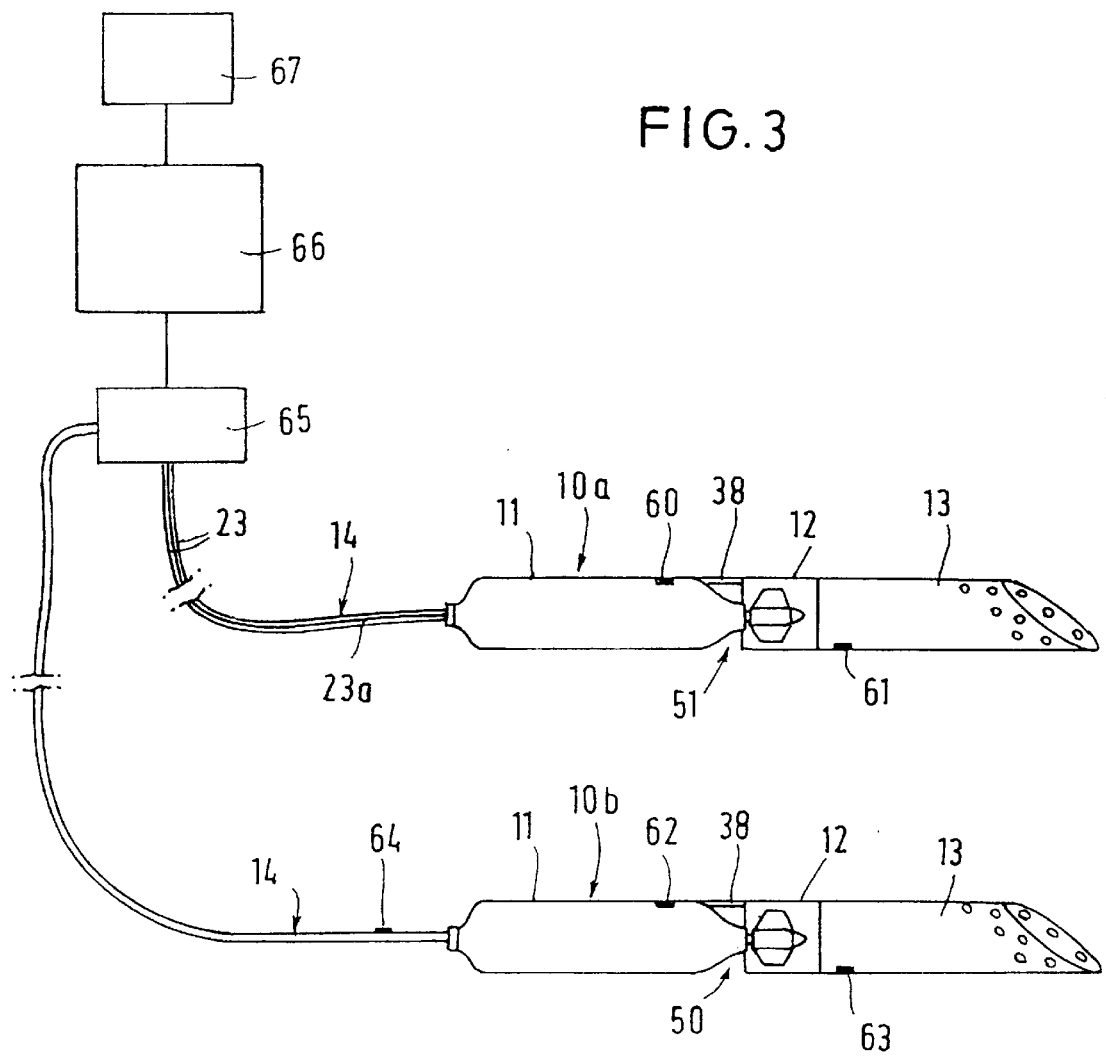
Figure 4:
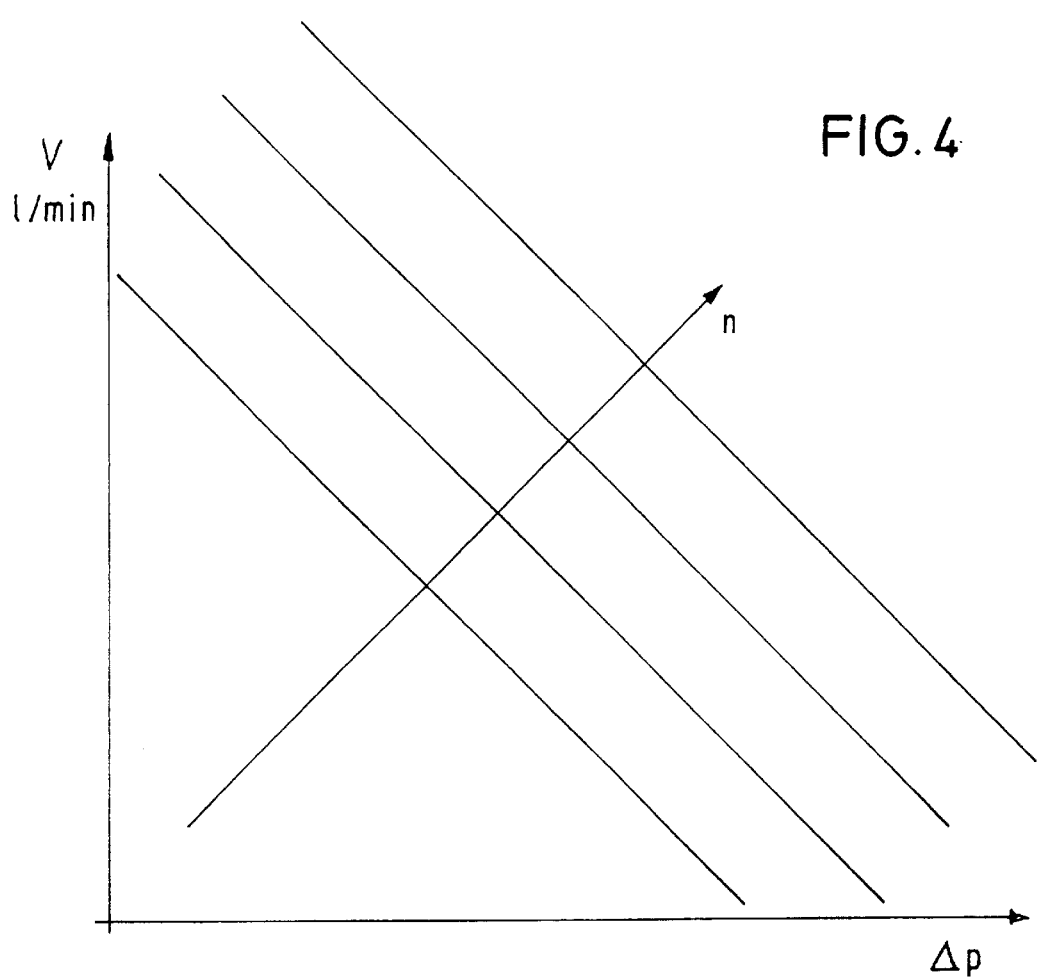
Figure 5:
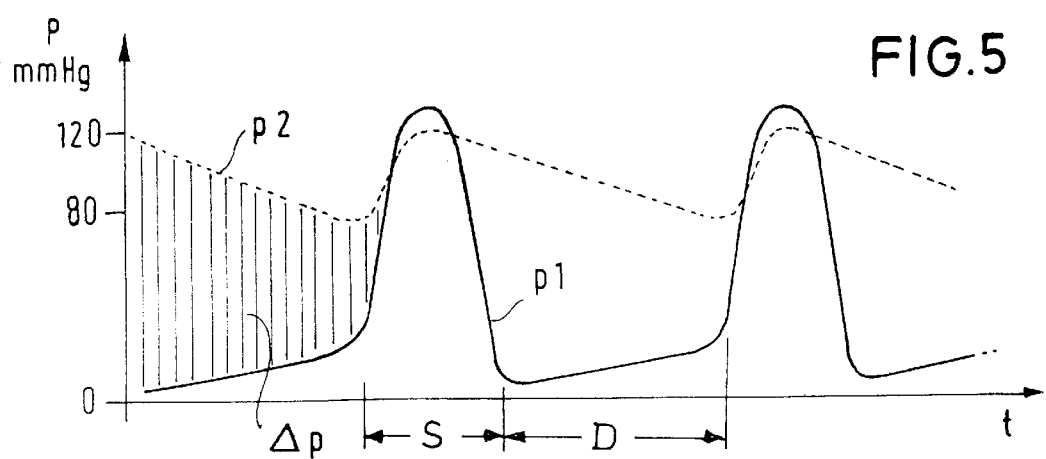
Figure 6:
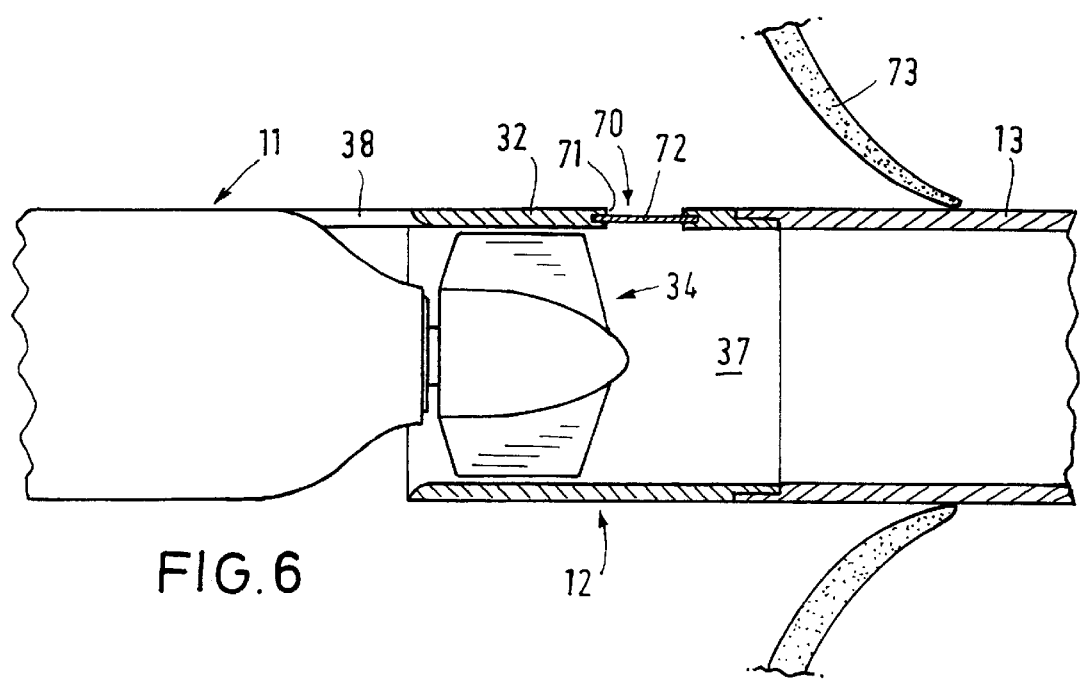
Figure 7:
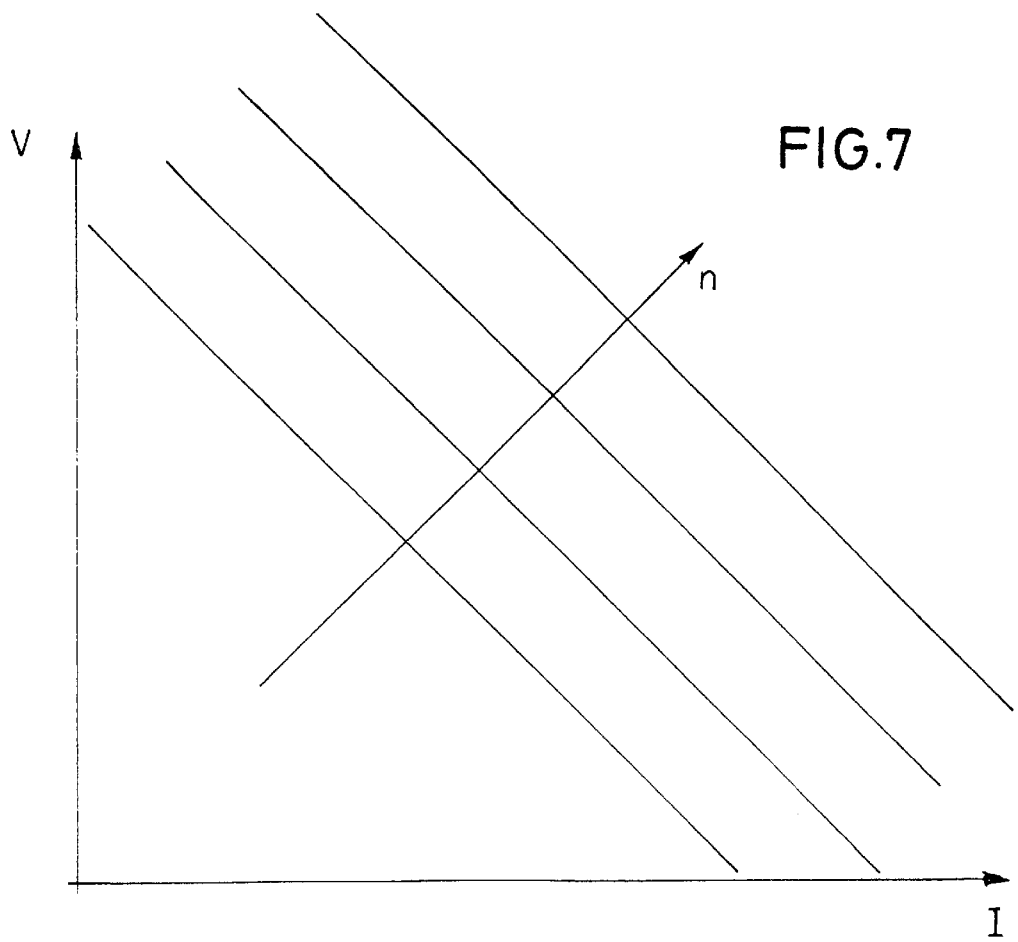

In the Figures:

FIG. 1 illustrates a schematic longitudinal section of one embodiment of an intracardiac blood pump, FIG. 2 shows an embodiment of the intracardiac implementation of two intravascular pumps, FIG. 3 is a schematic diagram for explaining a pump system, FIG. 4 is a diagram for showing the dependance of the volume flow on the differential pressure between the intake side and the delivery side of a pump, FIG. 5 shows a diagram of the variation in time of different pressures in the heart, FIG. 6 illustrates a longitudinal section of a part of the blood pump comprising a differential pressure sensor, and FIG. 7 is a diagram for showing the dependance of the volume flow on the motor current and the rotational speed.

FIG. 1 shows an intravascular blood pump 10, i.e. a blood pump that may be pushed through the blood vessel system of a patient to eventually arrive in the heart. The outer diameter of such a pump is nowhere larger than 7 mm.

The pump 10 comprises a drive portion 11 and a rigidly connected pump portion 12. The drive portion 11 has an elongated cylindrical housing 20 accommodating an electric motor 21. At the rear end, the housing 20 is closed with an end wall 22 which is followed by a flexible catheter 14 sealing the same. The electric lines 23 for power supply and for controlling the electric motor 21 and further lines 23a connected to the sensors of the pump 10 extend through this catheter 14.

As is typical, the stator 24 of the motor has a plurality of circumferentially distributed coils and a magnetic yoke arranged in the longitudinal direction. It is firmly connected to the motor housing 20. The stator 24 surrounds the rotor 26 that is connected with the motor shaft 25 and is made of permanent magnets magnetized in the effective/active direction. A bearing 27 supports the rear end of the motor shaft in the motor housing or the end wall 22. The motor shaft extends throughout the entire length of the motor housing 20 and projects therefrom to the front.

The front closure of the motor housing is formed by a tubular stationary hub member 30 having its rear end located in a reduced diameter projection 20a of the housing 20. The outer diameter of the hub member tapers towards the front end where a bearing 33 for supporting the motor shaft 25 is situated. This bearing is simultaneously designed as a shaft seal.

The motor shaft 25 protrudes forward from the hub member 30, where it carries an impeller wheel 34 with a hub 35 sitting on the shaft end and blades 36 or pump vanes protruding therefrom and being oblique with respect to the axis of the impeller wheel 34. The impeller wheel 34 is accommodated in a cylindrical pump housing 32 connected with the motor housing 20 by three circumferentially distributed webs 38. The motor housing 20 and the pump housing 32 are rigidly interconnected by means of a ring 38 and have equal outer diameters. The diameter of the pump 10 is nowhere larger than this outer diameter.

When the impeller wheel 34 rotates, blood is drawn through the intake opening 37 of the pump housing 32 and forced rearward in the axial direction in the pump housing 32. Through the annular gap between the pump housing 32 and the motor housing 20, blood flows outward along the hub member 30 to further flow along the motor housing 20. Thereby, the heat generated in the drive is carried away without the blood being damaged by excessively high surface temperatures (above 41° C.) on the motor housing 20.

It is also possible to design the pump portion 12 for the opposite delivery direction, the blood being drawn along the motor housing and being discharged axially at the front end opening 27.

FIG. 2 illustrates an embodiment wherein two generally identical pumps 10a, 10b, configured as illustrated in FIG. 1, are used in a heart to support the heart or as a substitute for the pumping function of the heart when the heart is immobilized. Both pumps 10a, 10b are connected with a catheter 14a, 14b, respectively. They have been placed percutaneously, the catheter 14a of the left cardiac pump 10a extending through the aorta 40 and a hose 13 prolongating the pump 10a being advanced into the left ventricle 42 through the aortic valve 41. Here, the pump portion 12 is prolongated by the flexible hose 13 connected with the pump housing 32, the end and/or the side wall of the hose being provided with openings for blood to enter into the pump 10a. The pump 10a takes in through the hose 13 and delivers blood into the aorta 40, while the aortic valve 41 abuts on the pump housing 32 or the hose 13 from outside. Thus, in the left ventricle 42, the pump 10a is operated as a left heart pump with axial intake.

The other pump 10b is operated as a right heart pump in fluid communication with the right ventricle 43. The catheter 14b passes through the upper or the lower vena cava 44 into the right atrium 45. The hose 13 of the pump 10b projects through the tricuspidal valve 43a and the pulmonary valve 46 into the pulmonary artery 47 from where the blood flows to the lung 48 for oxygenizing. The oxygenized blood the flows into the left vestibule 49 and on into the left ventricle 42.

The pump 10b takes in through the radial inlet 50 and conveys blood through the hose 13 axially into the pulmonary artery 47. Thus, the pump 10b is operated inversely to the pump 10a.

Both pumps 10a, 10b are introduced into the heart without one of the ventricles having to be surgically opened.

FIG. 3 is a schematic illustration of the two pumps 10a, 10b with different sensors. Specifically, the outer surface of the drive unit 11 is provided with a first pressure sensor 60 located close to the radial opening 51, whereas a second pressure sensor 61 is arranged near the inlet of the pump housing. The lines 23a of the sensors are integrated into the elements of the pump and extend through the catheter 14 together with the supply lines 23. The sensor surface of the pressure sensor 60 is on the exterior of the motor housing. Conversely, the sensor face of the pressure sensor 61 is provided on the inner surface of the hose 13. Further, a temperature sensor may be provided at the drive portion for monitoring the motor temperature.

Similarly, in the pump 10b, a first pressure sensor 62 is provided on the outer surface of the motor housing and a further pressure sensor 63 is provided on the inner surface of the hose 13. The lines of these sensors also extend through the catheter 14. The catheter 14 is provided with an oxygen sensor 64 providing information on the oxygenation of the blood.

The supply lines 23 and the lines 23a are connected with an extracorporeal interface 65,. This interface supplies the signals from the sensors to a control unit 66 that evaluates these signals and controls the pumps 1a, 10b in dependence thereon. A keypad and display device 67 is connected with the control unit 66 to allow for information to be entered and displayed.

Using the information supplied by the sensors, it is possible to determine the position of a pump relative to an external enclosing member, e.g. a cardiac valve. When the pump inlet and the pump outlet are on different sides of the enclosing member, a differential pressure will appear at the pressure sensors due to the different pressure conditions. When the heart beats, this differential pressure also varies in time. On the other hand, equal measured pressure values indicate an incorrect positioning of the pump because both pressure sensors measure the same pressure. The evaluation of the data supplied by the two pressure sensors, with consideration to the motor current, provides important information on the positioning and the operation of the pump. By comparing the differential pressure to the momentaneous motor current, it is also possible to determine blocking conditions or cavitation.

Information on the inlet and outlet pressures of the pump, together with the energy consumption of the electric motor, provide important statements on the functioning of a pump device. They also supply a real time indication on the volume flow and allow for the pump to be positioned without x-ray or ultrasonic control. Moreover, a real time monitoring of an impeded inlet flow can be effected, as may be caused, e.g., by a collapse of the ventricle, thrombogenesis, occlusion of the hose or by cardiac tissue being drawn in. Further, the sensors make it possible to monitor the wearing of bearings, of failures of the motor or to predict such events. Furthermore, the operation of the pump can be maintained with acceptable total hemolysis rates for the required period of use and with the required volume flow of 3.6 to 5 l/min. The performance trends of various parameters may be displayed and analyzed for several hours of operation, with alarm conditions that require immediate intervention being detected without necessitating permanent control by personnel. Further, the heart of a patient can be monitored without removing the pump. When placing two instrumented pumps, to supply the control unit with the local information provided by one pump so as to control the operation of the other pump, thereby optimizing the performance of the overall system.

The control unit 66 controls both pumps 10a, 10b such that each pump delivers a certain volume flow (volume of blood per unit time). In doing so, the right heart pump 10b pumps a predetermined percentage of the volume flow of the left heart pump 10a, for example 90%. The volume flow of the right heart pump is always smaller than that of the left heart pump. Primarily, the pumping capacity of the left heart pump 10a is controlled such that a predetermined volume flow is maintained. Subsequently, the pumping capacity of the right heart pump 10b is determined as a function thereof. This is a master-slave operation, where usually the left heart pump 10a is the master and the right heart pump 10b is the slave.

The pumps are driven by synchronous motors, with the control unit 66 supplying the required drive frequency or rotational speed n. The volume flow of each pump is a function of the rotational speed n.

FIG. 4 illustrates the volume flow V of a pump in dependance on the differential pressure ΔP between the intake side and the delivery side of the pump for respective different rotational speeds n. Each parallel straight line relates to a specific rotational speed n. It is evident that the volume flow V may be calculated from the differential pressure ΔP when the rotational speed n is known. The motor 21 is an electronically commutated synchronous motor. Since the rotational speed is preset by the control unit, the rotational speed is known. The differential pressure ΔP is determined by means of the sensors 60 and 61 or 62 and 63, respectively. Moreover, of course, the absolute values of the pressures are measured and evaluated as well.

When a pump takes in through the radial intake opening 50 or 51 and delivers into the hose 13, the pressure at the hose-side pressure sensor 61 or 63 is greater than at the intake-side pressure sensor 60 or 62. However, when the pump pumps in the opposite direction, i.e. when it takes in through the hose 13, the pressure at the pressure sensor 60 or 62 is greater than the pressure at the pressure sensor 61 or 63, respectively.

It can happen that one of the pumps is entirely or partly occluded by the pump getting sucked to cardiac tissue or the valve apparatus. In this case, the pressure sensors supply abnormal values. The rotational speed of the respective pump will then be reduced for a ceratin time so that the cardiac tissue may disengage itself, and, subsequently, the rotational speed will be increased again to the desired number. When the measured absolute pressure becomes too high, the control unit 66 will effect a limitation—and, if need be, a reduction—of the volume flow to avoid damage to downstream organs (lungs).

Measuring the pressure also provides a watch function. The pressure in the right ventricle or in the pulmonary artery must not exceed a certain value, and the pressure in the left ventricle or in the aorta must not fall below a certain pressure. When corresponding pressure deviations are detected, an alarm is emitted or an adjustment is effected.

FIG. 5 illustrates the pressure variation p1 in the left ventricle of the beating heart with the systoles S and the diastoles D. One can see a strongly pulsating pressure that drops sharply between systoles S. Moreover, the pressure variation p2 in the aorta is illustrated. The aortic pressure may also pulsate, yet it does so in a much narrower pressure range. The differential pressure ΔP is determined from p–p1. This differential pressure may be determined with the pressure sensors provided on the pumps.

Measuring the pressures and the differential pressures is important in particular for the insertion of the pump into the correct position in the heart. The insertion may be done with the pump at a standstill or running at a low rotational speed while the heart is beating. When one pressure sensor detects the strongly pulsating pressure variation p1 and the other detects the weakly pulsating pressure variation p2, the pump is positioned correctly.

However, measuring the pressure is not necessary for positioning. Rather, the positioning may also be monitored by means of the current variation of the pump. As long as the inlet and the outlet of a pump are in the same space, both are subjected to the same pressure. If the pump is driven with a certain rotational speed, the variation in time of the pump current is constant. If, however, the outlet and the inlet of the pump are in different spaces with pressures varying in time, no smooth, but a pulsating pump current will be obtained. Thus, it can be determined on the basis of the pump current, whether the cardiac valve correctly encloses the pump housing or the hose so that the inlet of the pump is located in the ventricle or the vestibule and the outlet is in the aorta or the pulmonary artery.

The sensors 61, 62 described above are absolute pressure sensors. FIG. 6 illustrates an embodiment comprising a differential pressure sensor 70 arranged in an opening 71 in the wall of the pump housing 32. The differential pressure sensor 70 has a flexible membrane 72 carrying electric resistance elements (not illustrated), the resistance of which depends on the deformation of the membrane 72. When the pump takes in via the opening 37, the inlet pressure of the pump acts on the lower surface of the membrane 72. The outlet pressure of the pump acts on the outer surface of the membrane 72. It is assumed that a cardiac valve 73 abuts against the outside of the hose 13. When the hose 13 is passed through the cardiac valve 73, a differential pressure occurs at the differential pressure sensor 70. If, however, the entire pump is in the same chamber, no substantial differential pressure occurs at the pressure sensor. By evaluating the signal from the differential pressure sensor 70, one may thus determine, whether the blood pump is in the correct position.

However, determining the position of the blood pump in the heart does not require a pressure measuring device at all. All that is needed is a measuring device that supplies an information signal corresponding to the differential pressure between the outlet side and the inlet side of the pump. This measuring device may be a device measuring the motor current of the motor driving the pump. The diagram of FIG. 7, similar to that of FIG. 4, illustrates the volume flow V of a pump as a function of the current I of the motor driving this pump for different rotational speeds n, respectively. Each of the parallel straight lines relates to a certain rotational speed n. It is evident that the volume flow V may be determined from the amount of the current I, when the rotational speed n is known. Thus, the volume flow V may be determined by simply measuring the current. Moreover, the correct position of the pump in the heart can also be verified by measuring the current.

When the heart is beating and the blood pump is positioned as the blood pump 10a shown in FIG. 2, the pulsating pressure designated P1 in FIG. 5 is caused in the ventricle 42 at the inlet of the blood pump. On the other hand, the less pulsating pressure P2 of FIG. 5 is generated at the pump outlet. In this case, the differential pressure ΔP is a pulsating value. If, on the other hand, the blood pump is entirely located in the aorta, the pressure difference between the inlet and the outlet of the pump is substantially zero. The same is true when the blood pump is entirely located in the left ventricle 42. Thus, by measuring the pulsating differential pressure ΔP (FIG. 5), the correct position of the pump may be determined.

Comparing the diagrams of FIGS. 4 and 7, it is evident that, for constant rotational speeds, the current I consumed by the motor is proportional to the differential pressure ΔP. If a pulsating differential pressure ΔP is obtained, the motor current I is also pulsating. Thus, the pulsation of the motor current I helps in determining, when the correct pump position is reached. In this case, the variation of the current I may be used as an information signal.

The invention allows to control the pump operation so as to obtain a desired volume flow as a function of the result of a pressure measurement or the result of a current measurement. These measurements may be taken in a very simple manner without voluminous measuring devices so that the operation of the pump may be accurately monitored, despite the compact structure.

What is claimed is:

1. An intracardiac blood pump comprising a drive portion (11) with a motor (21), and a pump portion (12) rigidly connected with the drive portion, the drive portion and the pump portion having substantially the same diameter and being arranged coaxially with a mutual axial distance, and comprising a pressure measuring device, characterized in that the pressure measuring device comprises a fist pressure sensor (60) measuring the pressure at an outlet side of the pump and a second pressure sensor (61) measuring the pressure at an inlet side of the pump and means that calculate the differential pressure between the outlet side and the inlet side of the pump from the signals of both pressure sensors (60,61), and that a control unit (66) controls the rotational speed of the motor (21) as a function of a signal from the pressure measuring device.

2. The blood pump of one of claim 1, characterized in that the drive portion (11) is provided with a temperature sensor that triggers an alarm upon reaching a predetermined temperature.

3. An intracardiac blood pump comprising a drive portion (11) with a motor (21), and a pump portion (12) rigidly connected with the drive portion, the drive portion and the pump portion having substantially the same diameter and being arranged coaxially with a mutual axial distance, and comprising a pressure measuring device characterized in that the pressure measuring device comprises a differential pressure sensor (70) measuring the differential pressure between an outlet side and an inlet side of the pump and that a control unit (66) controls the rotational speed of the motor (21) as a function of a signal from the pressure measuring device.

4. The blood pump of claim 3, characterized in that the pressure measuring device comprises a current measuring device for measuring the motor current (I) and for determining the differential pressure between the outlet side and the inlet side of the motor from the motor current (I) and the rotational speed (n).

5. The blood pump of claim 3, characterized in that the drive portion (11) is provided with a temperature sensor that triggers an alarm upon reaching a predetermined temperature.

6. An intracardiac blood pump comprising a drive portion (11) with a motor (21), and a pump portion (12) rigidly connected with the drive portion, the drive portion and the pump portion having substantially the same diameter and being arranged coaxially with a mutual axial distance, and comprising a pressure measuring device, characterized in that the pressure measuring device comprises a current measuring device for measuring the motor current (I) and for determining the differential pressure between the outlet side and the inlet side of the motor from the motor current (I) and the rotational speed (n) and that a control unit (66) controls the rotational speed of motor (21) as a function of a signal from the pressure measuring device.

7. The blood pump of claim 6, characterized in that the drive portion (11) is provided with a temperature sensor that triggers an alarm upon reaching a predetermined temperature.

8. An intracardiac blood pump comprising a drive portion (11) with a motor (21), and a pump portion (12) rigidly connected with the drive portion, the drive portion and the pump portion having substantially the same diameter and being arranged coaxially with a mutual axial distance, and comprising a measuring device, characterized in that the measuring device supplies an information signal corresponding to the differential pressure between the outlet side and the inlet side of the pump, and that a display device is provided that, depending on the variation in time of the information signal, supplies information on the correct positioning of the pump in the heart.

9. An intracardiac blood pump comprising a drive portion (11) with a motor (21), and a pump portion (12) rigidly connected with the drive portion, the drive portion and the pump portion having substantially the same diameter and being arranged coaxially with a mutual axial distance, and comprising a measuring device, characterized in that the measuring device supplies an information signal corresponding to the differential pressure between the outlet side and the inlet side of the pump, and that a control unit (66) controls the rotational speed of the motor (21) as a function of the information signal.

10. The blood pump of claim 8 or 9, characterized in that the information signal is derived from the differential pressure given by two pressure sensors (60,61) or from he signal from one differential pressure sensor (70).

11. The blood pump of claim 8 or 9, characterized in that the information signal is derived from the motor current (I).

12. The blood pump of claim 11, characterized in that the drive portion (11) is provided with a temperature sensor that triggers an alarm upon reaching a predetermined temperature.

13. The blood pump of claim 10, characterized in that the drive portion (11) is provided with a temperature sensor that triggers an alarm upon reaching a predetermined temperature.

* * * * *

UNITED STATES PATENT AND TRADEMARK OFFICE
CERTIFICATE OF CORRECTION

PATENT NO.   : 6,176,822 B1
DATED        : January 23, 2001
INVENTOR(S)  : Christopher Nix and Thorsten Siess Page 1 of 1

It is certified that error appears in the above-identified patent and that said Letters Patent is hereby corrected as shown below:

<u>Column 6,</u>
Line 22, replace "p-p1" with -- p2-p1 --.

Signed and Sealed this

Twenty-seventh Day of November, 2001

Attest:

*Nicholas P. Godici*

NICHOLAS P. GODICI
*Attesting Officer*   *Acting Director of the United States Patent and Trademark Office*